United States Patent
Seitz et al.

(10) Patent No.: US 6,774,086 B2
(45) Date of Patent: Aug. 10, 2004

(54) 3-AMINOCARBONYL-SUBSTITUTED BENZOYLCYCLOHEXANEDIONES

(75) Inventors: Thomas Seitz, Viernheim (DE); Lothar Willms, Hofheim (DE); Andreas van Almsick, Karben (DE); Hermann Bieringer, Eppstein (DE); Thomas Auler, Bad Soden (DE); Hubert Menne, Hofheim Ts. (DE)

(73) Assignee: Bayer CropScience GmbH, Frankfurt (DE)

( * ) Notice: Subject to any disclaimer, the term of this patent is extended or adjusted under 35 U.S.C. 154(b) by 26 days.

(21) Appl. No.: 10/238,155

(22) Filed: Sep. 10, 2002

(65) Prior Publication Data

US 2003/0191027 A1 Oct. 9, 2003

(30) Foreign Application Priority Data

Sep. 11, 2001 (DE) ......................................... 101 44 529

(51) Int. Cl.[7] ..................... C07D 207/06; C07D 211/32; C07D 295/08; A01N 43/40; A01N 43/36
(52) U.S. Cl. ....................... 504/224; 504/247; 504/249; 504/284; 504/287; 504/338; 504/336; 504/348; 548/530; 548/494; 546/146; 546/165; 546/226; 544/160; 544/162; 544/176; 568/329
(58) Field of Search ................................. 548/530, 494; 546/146, 165, 226; 544/160, 162, 176; 568/329; 504/226, 247, 249, 284, 287, 338, 336, 348

(56) References Cited

FOREIGN PATENT DOCUMENTS

| | | |
|---|---|---|
| AT | 200131666 | 7/2001 |
| EP | 0319075 | 6/1989 |
| WO | WO 90/05712 | 5/1990 |
| WO | 92/07837 | 5/1992 |
| WO | 96/22958 | 8/1996 |
| WO | 98/42648 | 10/1998 |
| WO | 99/10327 | 3/1999 |
| WO | 01/32636 | 5/2001 |
| WO | WO 01/53275 | 7/2001 |

OTHER PUBLICATIONS

English translation of WO 01/32636 (May 10, 2001).

English language abstract of WO 99/10327 (Mar. 4, 1999).

*Primary Examiner*—Mark L. Berch
*Assistant Examiner*—Kahsay Habte
(74) *Attorney, Agent, or Firm*—Connolly Bove Lodge and Hutz LLP

(57) ABSTRACT

There are described derivatives of benzoylcyclohexanediones of the formula (I) and their use as herbicides.

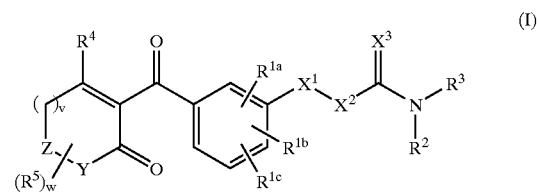

In this formula (I), $R^{1a}$, $R^{1b}$, $R^{1c}$, $R^2$, $R^3$, $R^4$ and $R^5$ are various radicals, $X^1$ is a bridging atom, $X^2$ a carbon chain and $X^3$ a chalcogen atom.

18 Claims, No Drawings

3-AMINOCARBONYL-SUBSTITUTED BENZOYLCYCLOHEXANEDIONES

The invention relates to the technical field of the herbicides, in particular that of the herbicides from the benzoylcyclohexanedione group, for the selective control of broad-leaved weeds and grass weeds in crops of useful plants, in particular in rice crops.

It has already been disclosed in a variety of publications that certain benzoylcyclohexanediones have herbicidal properties. Thus, EP-A 0 319 075, WO 92/07837 and WO 96/22958 disclose benzoylcyclohexandiones with a haloalkoxy radical in the 3-position of the phenyl ring. WO 98/42648 mentions benzoylcyclohexanediones which have a variety of amino radicals attached to them in the 3-position. WO 99/10327 and WO 01/32636 describe herbicidally active benzoyl-cyclohexanediones with a heterocyclic substituent in the 3-position, which is bonded via an oxygen-carbon bridge.

However, the herbicidal activity of the compounds known from these publications is frequently insufficient. It is therefore an object of the present invention to provide herbicidally active compounds whose herbicidal properties are improved over the compounds disclosed in the prior art.

It has now been found that derivatives of benzoylcyclohexanediones whose phenyl ring has certain radicals from the aminocarbonylalkyl group attached to it in the 3-position—bonded to the phenyl ring via an atom selected from the group consisting of oxygen, sulfur and nitrogen—are particularly suitable as herbicides. The present invention therefore relates to compounds of the formula (I) or salts thereof

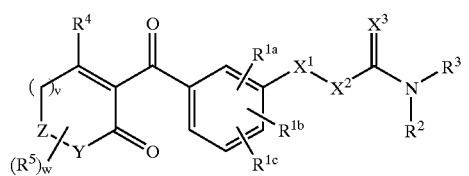

in which
X$^1$ is a divalent unit selected from the group consisting of O, S(O)$_n$, N—H and N—R$^2$;
X$^2$ is a straight-chain or branched (C$_1$–C$_6$)-alkylene, (C$_2$–C$_6$)-alkenylene or (C$_2$–C$_6$)-alkynylene chain which is substituted by w radicals selected from the group consisting of halogen, cyano and nitro and by v radicals R$^2$;
X$^3$ is oxygen or sulfur;
R$^{1a}$, R$^{1b}$, R$^{1c}$ independently of one another are hydrogen, mercapto, nitro, halogen, cyano, thiocyanato, (C$_1$–C$_6$)-alkyl-CO—O, (C$_1$–C$_6$)-alkyl-S(O)$_n$—O, (C$_1$–C$_6$)-alkyl-S(O)$_n$, di-(C$_1$–C$_6$)-alkyl-NH—SO$_2$, (C$_1$–C$_6$)-alkyl-SO$_2$—NH, (C$_1$–C$_6$-alkyl-NH—CO, (C$_1$–C$_6$)-alkyl -SO$_2$—[(C$_1$–C$_6$)-alkyl]amino,(C$_1$–C$_6$)-alkyl-CO-[(C$_1$–C$_6$)-alkyl]amino, 1,2,4-triazol-1-yl, (C$_1$–C$_6$)-alkyl-O—CH$_2$, (C$_1$–C$_6$)-alkyl-S(O)$_n$—CH$_2$, (C$_1$–C$_6$)-alkyl-NH—CH$_2$, 1,2,4-triazol-1yl-CH$_2$, or are (C$_1$–C$_6$)-alkyl-(D)$_p$, (C$_2$–C$_6$)-alkenyl-(D)$_p$, (C$_2$–C$_6$)-alkynyl-(D)$_p$, (C$_3$–C$_9$) -cycloalkyl-(D)$_p$, (C$_3$–C$_9$)-cycloalkenyl-(D)$_p$, (C$_1$–C$_6$)-alkyl-cycloalkyl-(D)$_p$, (C$_1$–C$_6$)-alkyl-cycloalkenyl-(D)$_p$, each of which is substituted by v radicals selected from the group consisting of cyano, nitro and halogen;
D is oxygen or sulfur;

R$^2$, R$^3$ independently of one another are hydrogen, (C$_1$–C$_6$)-alkyl, (C$_2$–C$_6$)-alkenyl, (C$_2$–C$_6$)-alkynyl, (C$_3$–C$_9$)-cycloalkyl, (C$_3$–C$_9$)-cycloalkenyl, (C$_1$–C$_6$)-alkyl-(C$_3$–C$_9$)-cycloalkyl, (C$_1$–C$_6$)-alkyl-(C$_3$–C$_9$)-cycloalkenyl, (C$_2$–C$_6$)-alkenyl-(C$_3$–C$_9$)-cycloalkyl, (C$_2$–C$_6$)-alkenyl-(C$_3$–C$_9$)-cycloalkenyl, (C$_2$–C$_6$)-alkynyl-(C$_3$–C$_9$)-cycloalkyl, (C$_2$–C$_6$)-alkynyl-(C$_3$–C$_9$)-cycloalkenyl, straight-chain or branched [O—C(R$^6$)$_2$]$_w$-[O—C(R$^6$)$_2$]$_x$-R$^6$, (C$_1$–C$_6$)-alkylaryl, (C$_2$–C$_6$)-alkenylaryl, (C$_2$–C$_6$)-alkynylaryl, straight-chain or branched [O—C(R$^6$)$_2$]$_w$-[O—C(R$^6$)$_2$]$_x$-aryl, the abovementioned carbon-containing radicals being substituted by v radicals selected from the group consisting of cyano, nitro and halogen,
aryl, heterocyclyl or heteroaryl, each of which is substituted by v radicals selected from the group consisting of cyano, nitro, halogen, (C$_1$–C$_6$)-alkyl-(D)$_p$ and halo-(C$_1$–C$_6$)-alkyl-(D)$_p$,
or
R$^2$ and R$^3$ together with the nitrogen atom to which they are bonded form a 5- or 6-membered, saturated, partially or fully unsaturated ring comprising m hetero atoms selected from the group consisting of oxygen and nitrogen, the 5- or 6-membered ring optionally being benzo-fused to a phenyl ring and being substituted by v radicals selected from the group consisting of cyano, nitro, halogen, (C$_1$–C$_6$)-alkyl-(D)$_p$ and halo-(C$_1$–C$_6$)-alkyl-(D)$_p$ and the fused phenyl ring being substituted by v radicals selected from the group consisting of cyano, nitro and halogen;
R$^4$ is OR$^7$, (C$_1$–C$_4$)-alkylthio, halo-(C$_1$–C$_4$)-alkylthio, (C$_2$–C$_4$)-alkenylthio, halo-(C$_2$–C$_4$)-alkenylthio, (C$_2$–C$_4$)-alkynylthio, halo-(C$_2$–C$_4$)-alkynylthio, (C$_1$–C$_4$)-alkylsulfinyl, halo-(C$_1$–C$_4$)-alkylsulfinyl, (C$_2$–C$_4$)-alkenylsulfinyl, halo-(C$_2$–C$_4$)-alkenylsulfinyl, (C$_2$–C$_4$)-alkynylsulfinyl, halo-(C$_2$–C$_4$)-alkynylsulfinyl, (C$_1$–C$_4$)-alkylsulfonyl, halo-(C$_1$–C$_4$)-alkylsulfonyl, (C$_2$–C$_4$)-alkenylsulfonyl, halo-(C$_2$–C$_4$)-alkenylsulfonyl, (C$_2$–C$_4$)-alkynylsulfonyl, halo-(C$_2$–C$_4$)-alkynylsulfonyl, halogen, cyano, cyanato, thiocyanato or phenylthio;
R$^5$ is hydrogen, tetrahydropyran-3-yl, tetrahydropyran-4-yl, tetrahydrothiopyran-3-yl, (C$_1$–C$_4$)-alkyl, (C$_1$–C$_8$)-cycloalkyl, (C$_1$–C$_4$)-alkoxy, (C$_1$–C$_4$)-alkoxy-(C$_1$–C$_4$)-alkyl, (C$_1$–C$_4$)-alkoxycarbonyl, (C$_1$–C$_4$)-alkylthio, phenyl, the eight last-mentioned groups being substituted by v radicals selected from the group consisting of halogen, (C$_1$–C$_4$)-alkylthio and (C$_1$–C$_4$)-alkoxy,
or
two radicals R$^5$ bonded to a joint carbon atom form a chain selected from the group consisting of OCH$_2$CH$_2$O, OCH$_2$CH$_2$CH$_2$O, SCH$_2$CH$_2$S and SCH$_2$CH$_2$CH$_2$S, this chain being substituted by w methylene groups, or two radicals R$^5$ bonded to directly adjacent carbon atoms, together with the carbon atoms bearing them, form a 3- to 6-membered ring which is substituted by w radicals selected from the group consisting of halogen, (C$_1$–C$_4$)-alkyl, (C$_1$–C$_4$)-alkylthio and (C$_1$–C$_4$)-alkoxy;
R$^6$ is hydrogen, halogen, cyano or nitro, (C$_1$–C$_4$)-alkyl, halo-(C$_1$–C$_4$)-alkyl;
R$^7$ is hydrogen, (C$_1$–C$_4$)-alkyl, halo-(C$_1$–C$_4$)-alkyl, (C$_1$–C$_4$)-alkoxy-(C$_1$–C$_4$)-alkyl, formyl, (C$_1$–C$_4$)-alkylcarbonyl, (C$_1$–C$_4$)-alkoxycarbonyl, (C$_1$–C$_4$)-alkylaminocarbonyl, di-(C$_1$–C$_4$)-alkylaminocarbonyl, (C$_1$–C$_4$)-alkylsulfonyl, halo-(C$_1$–C$_4$)-alkylsulfonyl, phenyl, benzoyl or phenylsulfonyl, the three last-mentioned groups being substituted by v radicals selected from the group consisting of ($C_1$–$C_4$)-alkyl, halo-($C_1$–$C_4$)-alkyl, ($C_1$–$C_4$)-alkoxy, halo-($C_1$–$C_4$)-alkoxy, halogen, cyano and nitro;

Y is a divalent unit selected from the group consisting of O, S, N—H, N—($C_1$–$C_6$)-alkyl, $CHR^5$ and $C(R^5)_2$;

Z is a direct bond or a divalent unit selected from the group consisting of O, S, SO, $SO_2$, N—H, N-alkyl, $CHR^6$ or $C(R^6)_2$;

m and n in each case independently of one another are 0, 1 or 2;

p is independently 0 or 1;

v is independently 0, 1, 2 or 3;

w and x in each case independently of one another are 0, 1, 2, 3 or 4, with the proviso that w and x are not simultaneously zero.

In the event that $R^4$ is OH, the compounds of the formula (I) according to the invention can exist in different tautomeric structures, depending on the external conditions such as solvent and pH. Depending on the nature of the substituents, the compounds of the formula (I) contain an acidic proton, which can be removed for example by reaction with a base. Examples of suitable bases are hydrides, hydroxides and carbonates of alkali and alkaline earth metals, such as lithium, sodium, potassium, magnesium and calcium, and also ammonia and organic amines such as triethylamine and pyridine. The invention likewise relates to such salts.

In formula (I) and all subsequent formulae, alkyl radicals with more than two carbon atoms can be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Likewise, the carbon chain $X^2$ can be straight-chain or branched, depending on the number of carbon atoms which it contains. The radicals bonded thereto can be in any desired position of this chain.

If a group is polysubstituted by radicals, this is understood as meaning that this group is substituted by one or more of the abovementioned radicals, which may be identical or different.

Cycloalkyl is a carbocyclic saturated ring system with three to eight carbon atoms, for example cyclopropyl, cyclopentyl or cyclohexyl. Analogously, cycloalkenyl is a monocyclic alkenyl group having three to eight carbon ring members, for example cyclopropenyl, cyclobutenyl, cyclopentyl and cyclohexenyl, it being possible for the double bond to be in any desired position. In the case of composite radicals, such as cycloalkylalkenyl, the first-mentioned radical may be in any desired position of the second-mentioned radical.

In the case of a disubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl, each of which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

The term heterocyclyl is understood as meaning three- to six-membered, saturated or partially unsaturated mono- or polycyclic heterocycles containing one to three hetero atoms selected from a group consisting of oxygen, nitrogen and sulfur. If chemically possible, the linkage can be effected at any desired position of the heterocycle. Examples are oxiranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothioazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxazolidin-2-yl, 1,3,4-thiadiazolidin-2-yl, 1,3,4-triazolidin-2- 2,3-dihydrofur-2-yl, 2,3-dihydrofur-3-yl 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 1-morpholinyl, 2-morpholinyl, 3-morpholinyl, 1-piperidinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,3-dithian-2-yl, 1,1-dioxo-2,3,4,5-tetrahydrothien-2-yl-2H-1,4-benzothiazin-3-yl, 2H-1,4-benzoxazin-3-yl, 1,3-dihydrooxazin-2-yl.

Aryl is an aromatic mono- or polycyclic hydrocarbon radical, for example phenyl, naphthyl, biphenyl and phenanthryl, preferably phenyl. In principle, the linkage may be effected at any desired position of the aryl.

Heteroaryl is an aromatic mono-, bi- or tricyclic radical which, in addition to carbon ring members, contains one to four nitrogen atoms or one to three nitrogen atoms and one oxygen or one sulfur atom or an oxygen or a sulfur atom. If chemically possible, the linkage can be effected at any desired position of the aryl. Examples of 5-membered heteroaryl are 2-pyrrolyl, 3-pyrrolyl, 1-pyrazolyl, 3-pyrazolyl, 4-pyrazolyl, 5-pyrazolyl, 2-imidazolyl, 4-imidazolyl, 1,2,4-triazol-3-yl, 1,3,4-triazol-2-yl, 2-furyl, 3-furyl, 2-thienyl, 3-thienyl, 2-pyrrolyl, 3-pyrrolyl, 3-isoxazolyl, 4-isoxazolyl, 5isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzofused 6-membered heteroaryl are quinoline, isoquinoline, quinazoline and quinoxaline.

If a group is polysubstituted, this is understood as meaning that, when the different substituents are combined, the general principles of the structure of chemical compounds must be observed, that is to say no compounds must be formed which are known to the skilled worker as being chemically unstable or impossible.

Depending on the type and linkage of the substituents, the compounds of the formula (I) can exist as stereoisomers. If, for example, one or more asymmetric carbon atoms are present, enantiomers and diastereomers may occur. Stereoisomers can be obtained from the mixtures resulting from the preparation by means of customary separation methods, for example by chromatographic separation methods. Likewise, stereoisomers may be prepared selectively by using stereoselective reactions and optically active starting materials and/or adjuvants. The invention also relates to all of the stereoisomers and their mixtures which are encompassed by the formula (I), but not defined specifically.

Compounds of the formula (I) which have proved advantageous are those in which $R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl-$(C_3-C_9)$-cycloalkyl, $(C_2-C_6)$-alkynyl-$(C_3-C_9)$-cycloalkenyl, straight-chain or branched $[O-C(R^6)_2]_w$-$[O-C(R^6)_2]_x$-$R^6$, the 12 last-mentioned radicals being substituted by v radicals selected from the group consisting of cyano, nitro and halogen, aryl which is substituted by v radicals selected from the group consisting of cyano, nitro, halogen, $(C_1-C_6)$-alkyl-$(D)_p$ and halo-$(C_1-C_6)$-alkyl-$(D)_p$ or $R^2$ and $R^3$ together with the nitrogen atom to which they are bonded form a 5- or 6-membered, saturated, partially or fully unsaturated ring comprising m hetero atoms selected from the group consisting of oxygen and nitrogen, which ring is substituted by v radicals selected from the group consisting of cyano, nitro, halogen, $(C_1-C_6)$-alkyl-$(D)_p$ and halo-$(C_1-C_6)$-alkyl-$(D)_p$;

$R^7$ is hydrogen, $(C_1-C_4)$-alkylsulfonyl, halo-$(C_1-C_4)$-alkylsulfonyl, phenyl, benzoyl or phenylsulfonyl, the three last-mentioned groups being substituted by v radicals selected from the group consisting of $(C_1-C_2)$-alkyl, halo-$(C_1-C_2)$-alkyl, $(C_1-C_2)$-alkoxy, halo-$(C_1-C_2)$-alkoxy, halogen, cyano and nitro;

Y is a divalent unit selected from the group consisting of O, N—H, N—$(C_1-C_6)$-alkyl, $CHR^5$ and $C(R^5)_2$, and Z is a divalent unit selected from the group consisting of O, S, $SO_2$, $(C_1-C_6)$-alkyl, $CHR^6$ or $C(R^6)_2$.

Likewise advantageous are compounds of the formula (I) in which $R^2$ is $(C_1-C_6)$-alkyl and $R^3$ is benzyl substituted by v radicals selected from the group consisting of cyano, nitro and halogen, or $R^2$ and $R^3$ together with the nitrogen atom to which they are bonded form a radical selected from the group consisting of 2,3-dihydroindol-1-yl, benzo[c]pyrrolidin-2-yl, 1,2,3,4-tetrahydroquinolin-1-yl and 1,2,3,4-tetrahydroisoquinolin-2-yl, each of which is substituted by v radicals selected from the group consisting of cyano, nitro and halogen.

Furthermore, advantageous compounds of the formula (I) are those in which $X^3$ is oxygen;

$R^{1c}$ is hydrogen, and $R^6$ is hydrogen, $(C_1-C_4)$-alkyl or halo-$(C_1-C_4)$-alkyl.

Preferred compounds of the formula (I) are those in which $X^1$ is oxygen;

$R^{1a}$ and $R^{1b}$ are in each case bromine, chlorine, fluorine, methyl, methylthio, methoxy, methylsulfonyl, ethylsulfonyl or trifluoromethyl, and $R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_1-C_6)$-alkyl-$(C_3-C_9)$-cycloalkyl, straight-chain or branched $[O-C(R^6)_2]_w$-$[O-C(R^6)_2]_x$-$R^6$, where the 6 last-mentioned radicals substituted by v radicals selected from the group consisting of cyano, nitro and halogen, are aryl which is substituted by v radicals selected from the group consisting of cyano, nitro, halogen, $(C_1-C_6)$-alkyl-$(D)_p$ and halo-$(C_1-C_6)$-alkyl-$(D)_p$, or $R^2$ and $R^3$ together with the nitrogen atom to which they are bonded form a 5- or 6-membered, saturated, partially or fully unsaturated ring comprising m hetero atoms selected from the group consisting of oxygen and nitrogen, which ring is substituted by v radicals selected from the group consisting of cyano, nitro, halogen, $(C_1-C_6)$-alkyl-$(D)_p$ and halo-$(C_1-C_6)$-alkyl-$(D)_p$.

Other preferred compounds of the formula (I) are those in which $R^4$ is $OR^7$, $(C_1-C_4)$-alkylthio, $(C_2-C_4)$-alkenylthio, $(C_1-C_4)$-alkylsulfonyl, halogen, cyano, cyanato, thiocyanato or phenylthio and $R^5$ is hydrogen, $(C_1-C_4)$-alkyl, $(C_1-C_8)$-cycloalkyl, $(C_1-C_4)$-alkoxy, $(C_1-C_4)$-alkylthio, phenyl, or two radicals $R^5$ bonded to directly adjacent carbon atoms together with the carbon atoms to which they are bonded form a substituted 3- to 6-membered ring.

Especially preferred compounds of the formula (I) are those in which the substituent $R^{1a}$ is in the 2-position of the substituent $R^{1b}$ is in the 4-position of the phenyl ring.

Very specially preferred compounds of the formula (I) are those in which $R^4$ is $OR^7$;

D is oxygen;

Y and Z are the group $CH_2$, and v and w in each case independently of one another are 0, 1 or 2.

Likewise very specially preferred compounds of the formula (I) are those which are not in salt form.

In all of the formulae stated hereinbelow, the substituents and symbols have the same meaning as defined under formula (I), unless otherwise defined.

Compounds according to the invention in which $R^7$ is hydrogen can be prepared for example in accordance with the method shown in scheme 1 by reacting, with base catalysis, a compound of the formula (IIIa) in which T is halogen, hydroxyl or alkoxy with a cyclohexanedione (II) in the presence of a cyanide source. Such methods are described, for example, in EP-A 0 186 117.

Scheme 1:

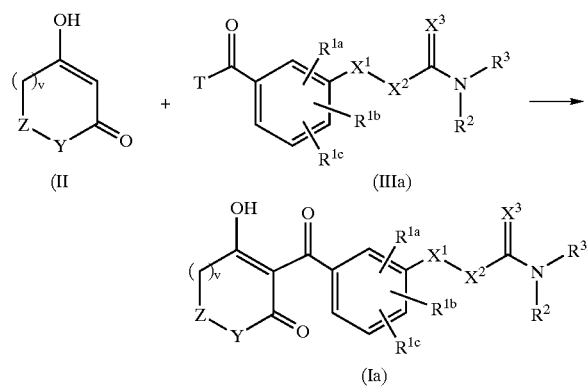

Compounds of the formula (IIIa) can be prepared for example in accordance with scheme 2 from compounds of the formula (IIIb) and (IVa) in which $L^2$ is a leaving group such as halogen, mesyl, tosyl or triflate, by methods known per se. Such methods are known for example from Houben-Weyl Volume 6/3, pp. 54 to 69, Volume 9, pp. 103 to 115 and Volume 11, p. 97.

Scheme 2:

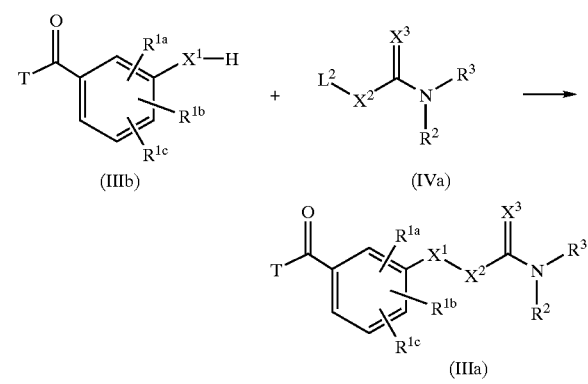

Compounds of the formula (IIIa) can also be prepared in accordance with scheme 3 by reacting compounds of the formula (IIIc) in which $L^3$ is a leaving group such as triflate or nonaflate with compounds of the formula (IVb). Such methods are known, for example, from WO 98/42648, Houben-Weyl Volume 6/3, pp. 75 to 78, and Volume 9, pp. 103 to 105.

Scheme 3:

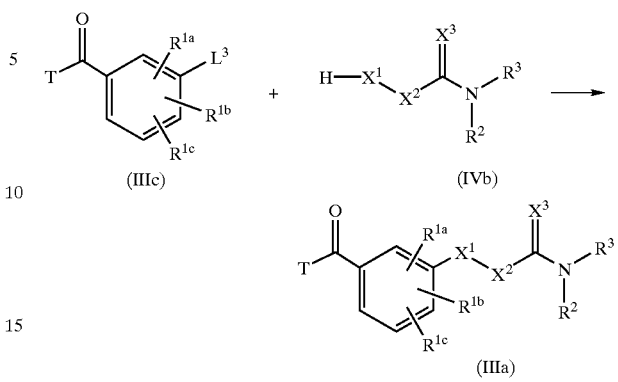

Likewise, compounds of the formula (IIIa) can be prepared in accordance with scheme 4 by reacting compounds of the formula (IIId) with compounds of the formula (V) in which $L^4$ is a leaving group such as halogen, mesyl, tosyl or triflate. Such methods are known, for example, from Houben-Weyl Volume 8, pp. 708 to 709, Volume 9, Volume E 5/2, pp. 998 to 1001 and 1213 to 1216.

Scheme 4:

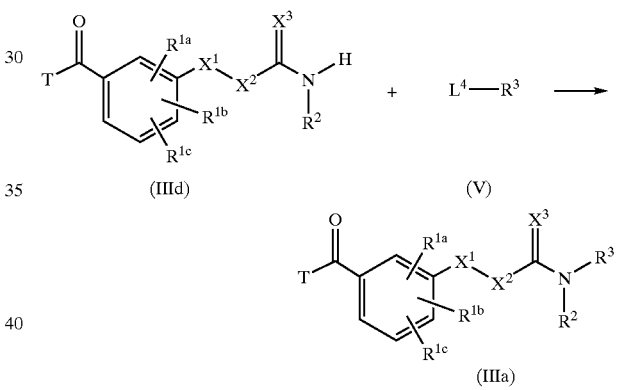

Compounds of the formula (IVa) can be prepared for example in accordance with scheme 5 by reacting compounds of the formula (VII) in which $L^3$ is a group such as chlorine or alkoxy and $L^2$ is a group such as chlorine, bromine, mesyl or tosyl with amines of the formula (VIII) by methods known per se. Such methods are known, for example, from Houben-Weyl Volume 8, pp. 647 to 660, Volume 11/2, pp.1 to 73 (in particular pp.10 to 14 and 20 to 23), Volume E 5/2, pp. 934 to 1135, and from J. Org. Chem. 39 (1974) pp. 2607 to 2612.

Scheme 5:

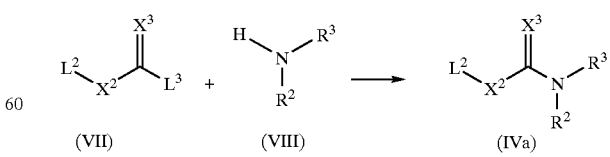

Compounds of the formula (IVb) can be prepared for example by the methods described in U.S. Pat. No. 4,264, 520, DE 3 222 229 and J. Med. Chem. 39 (1996) 26, pp. 5236 to 5245.

Compounds of the formula (I) according to the invention in which $R^4$ represents radicals other than hydroxyl can be prepared for example in accordance with scheme 4. The reaction of a compound of the formula (Ia) with a halogenating reagent such as oxalyl chloride or oxalyl bromide, which is shown in this scheme, yields compounds of the formula (Ib), according to the invention, which can be converted into further compounds of the formula (Ic) according to the invention in which $R^4$ is alkylthio, haloalkylthio, alkenylthio, haloalkenylthio, alkynylthio, haloalkynylthio, optionally substituted phenylthio, cyano, cyanato, thiocyanato or $OR^7$ by reaction with alkali metal cyanides, alkali metal cyanates, alkali metal thiocyanates, alkyl thioalcohols and thiophenols, if appropriate with base catalysis. Such reactions are described, for example, in Synthesis 12, 1287 (1992). The reaction with an oxidant, such as m-chloroperbenzoic acid, peroxyacetic acid, hydrogen peroxide and potassium peroxymonosulfate, gives compounds of the formula (Ic) according to the invention in which $R^4$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, optionally substituted phenylthio or haloalkynylsulfonyl. Such reactions are described, for example, in J. Org. Chem. 53, 532 (1988), Tetrahedron Lett. 21,1287 (1981).

perennial species. In the case of dicotyledonous weed species, the spectrum of action extends to species such as, for example, Galium, Viola, Veronica, Lamium, Stellaria, Amaranthus, Sinapis, Ipomoea, Sida, Matricaria and Abutilon from the annual group, and Convolvulus, Cirsium, Rumex and Artemisia among the perennials. Harmful plants which are found under the specific culture conditions of rice, such as, for example, Echinochloa, Sagittaria, Alisma, Eleocharis, Scirpus and Cyperus are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Amaranthus retroflexus*, Avena sp., Echinochloa sp., *Cyperus serotinus, Lolium multiflorum,*

Scheme 6:

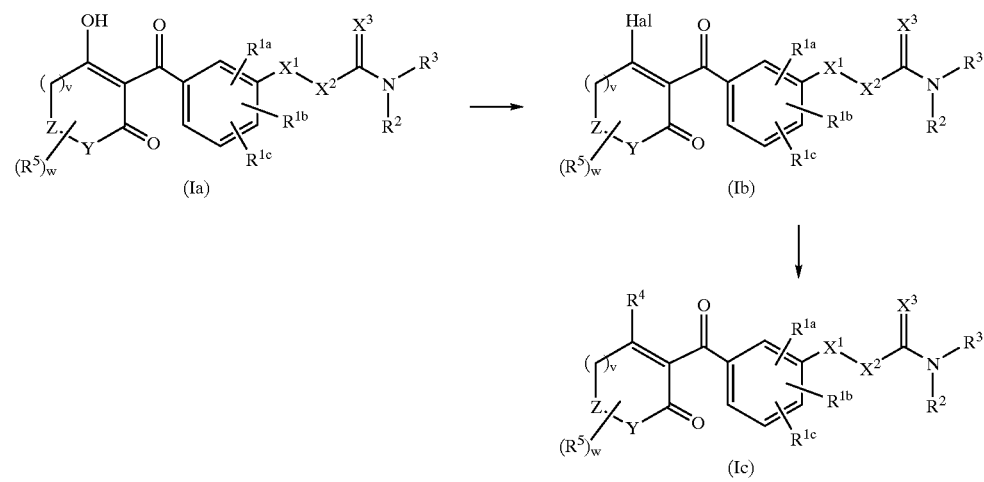

The compounds of the formula (I) according to the invention have an excellent herbicidal activity against a broad range of economically important monocotyledonous and dicotyledonous harmful plants. The active substances control perennial weeds equally well which produce shoots from rhizomes, root stocks or other perennial organs and which cannot be easily controlled. In this context, it does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, Avena, Lolium, Alopecurus, Phalaris, Echinochloa, Digitaria, Setaria and Cyperus species from the annual group, and Agropyron, Cynodon, Imperata and Sorghum or else perennial Cyperus species amongst the

*Setaria viridis, Sagittaria pygmaea, Scirpus juncoides*, Sinapis sp. and *Stellaria media*.

Although the compounds according to the invention have an outstanding herbicidal activity against monocotyledonous and dicotyledonous weeds, crop plants of economically important crops such as, for example, wheat, barley, rye, rice, maize, sugar beet, cotton and soy, only suffer negligible damage, if any. In particular, they are outstandingly well tolerated in wheat, maize and rice. This is why the present compounds are highly suitable for the selective control of undesired vegetation in stands of agricultural useful plants or of ornamentals.

Owing to their herbicidal properties, the active substances can be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or those whose fatty acid spectrum in the harvested material is different.

The compounds of the formula (I) according to the invention or their salts are preferably employed in economically important transgenic crops of useful plants and ornamentals, for example cereals such as wheat, barley, rye, oats, sorghum and millet, rice, cassava and maize, or else crops of sugar beet, cotton, soy, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability of producing *Bacillus thuringiensis* toxins (Bt toxins), which make the plants resistant to certain pests (EP-A-0142924, EP-A-0193259), transgenic crop plants with a modified fatty acid spectrum (WO 91/13972), A large number of techniques in molecular biology, with the aid of which novel transgenic plants with modified properties can be generated, are known in principle; see, for example, Sambrook et al., 1989, Molecular Cloning, A Laboratory Manual, $2^{nd}$ Ed., Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423–431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J.1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (=natural) genes or gene sequences or expressing heterologous (=foreign) genes or gene sequences.

When using the active substances according to the invention in transgenic crops, effects have frequently been observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally also have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil-or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDM, i.e. 2-chloro-N,N-di-2-propenylacetamide; CDEC, i.e. 2-chloroallyl diethyidithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro -5-oxo-1H-tetrazol-1yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl )sulfonyl]-1H-1,2,4-triazole-1-carboxamide; thenylchlor (NSK-850); triazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuronmethyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

The starting compound ethyl 2,4-dibromo-3-hydroxybenzoate was prepared as described in U.S. Pat. No. 5,026,896, and 2-chloro-3-hydroxy-4-ethylsulfonylbenzoic acid was prepared as described in EP-A 0 195 247.

The abbreviation RT stands for room temperature. $R_f$ is the retention value.

Process for the Preparation of 2-(2-chloro-3-(N,N-diethylaminocarbonylmethoxy)-4-ethylsulfonylbenzoyl)cyclohexane-1,3dione (tabulated example No. 3.10)

Step 1: Methyl 2-chloro-3-hydroxy-4-ethylsulfonylbenzoate 33.0 g (124.7 mmol) of 2-chloro-3-hydroxy-4-ethylsulfonylbenzoic acid were dissolved in 1 300 ml of methanol. 174 ml (3 263 mmol) of concentrated $H_2SO_4$ were added dropwise, and the mixture was refluxed for 5 hours. The reaction mixture was concentrated and the residue was taken up in $CH_2Cl_2$. The product was washed with water, dried over $Na_2SO_4$ and concentrated completely. This gave methyl 2-chloro-3-hydroxy-4-ethylsulfonylbenzoate as a yellow viscous oil.

Yield: 28.23 g (81% of theory) $R_f$: (ethyl acetate) 0.45

$^1$H NMR: δ [CDCl$_3$] 1.32 (t, 3H), 3.24 (q, 2H), 3.96 (s, 3H), 7.38 (d, 1H), 7.65 (d, 1H)

Step 2: Methyl 2-chloro-3-(N,N-diethylaminocarbonylmethoxy)-4-ethylsulfonyl-benzoate 0.922 g (7.2 mmol) of $K_2CO_3$, 0.179 g (1.10 mmol) of Kl and 0.644 g (4.3 mmol) of N,N-diethylchloroacetamide were introduced into 30 ml of DMF. 1.000 g (3.6 mmol) of methyl 2-chloro-3-hydroxy-4-ethylsulfonylbenzoate were added at RT and the mixture was then heated for 7 hours at 120° C. The mixture was then poured into water and extracted with diisopropyl ether. The organic phases were washed with water, dried over $Na_2SO_4$ and concentrated completely. Chromatography on silica gel (eluent: n-heptane/ethyl acetate 1:1) gave methyl 2-chloro-3-(N,N-diethylaminocarbonylmethoxy)-4-ethylsulfonylbenzoate as a colorless viscous oil.

Yield: 0.50 g (35% of theory)

$^1$H NMR: δ [CDCl$_3$] 1.07–1.29 (m, 9H), 3.16 (q, 2H), 3.45 (q, 2H), 3.69 (q, 2H), 3.96 (s, 3H), 4.90 (s, 2H), 7.68 (d, 1H), 7.92 (d, 1H)

Step 3: 2-Chloro-3-(N,N-diethylaminocarbonylmethoxy)-4-ethylsulfonylbenzoic acid 0.400 g (1.00 mmol) of methyl 2-chloro-3-(N,N-diethylaminocarbonylmethoxy)-4-ethylsulfonylbenzoate were dissolved in a mixture of 20 ml of THF and 20 ml of water, and 0.082 g (2.00 mmol) of NaOH was added. The mixture was stirred for 12 hours at room temperature and concentrated completely. The residue was taken up in water, 6 N HCl were added, and the mixture was extracted with $CH_2Cl_2$. Drying with $Na_2SO_4$ and concentrating the organic phase gave 2-chloro-3-(N,N-diethylaminocarbonylmethoxy)-4-ethylsulfonylbenzoate as a colorless viscous oil Yield: 0.37 g (99% of theory)

$^1$H NMR: δ [CDCl$_3$] 1.13–1.27 (m, 9H), 3.18 (q, 2H), 3.45 (q, 2H), 3.64 (q, 2H), 4.91 (s, 2H), 7.80 (d, 1H), 7.93 (d, 1H)

Step 4: 3-Oxo-1-cyclohexenyl 2-chloro-3-(N,N-diethylaminocarbonylmethoxy)-4-ethylsulfonylbenzoate 0.500 g (1.30 mmol) of 2-chloro-3-(N,N-diethylaminocarbonylmethoxy)-4-ethylsulfonylbenzoic acid, 0.163 g (1.30 mmol) of N'-(3-dimethylaminopropyl)-N-ethylcarbodiimide-hydrochloride and 0.002 g of DMAP were stirred for 10 hours at RT in 15 ml of $CH_2Cl_2$. The mixture was subsequently diluted with $CH_2Cl_2$ and washed with 0.5 N HCl, with water, with saturated NaHCO$_3$ solution and again with water. After the organic phases had been dried over $Na_2SO_4$ and concentrated completely, the product was obtained in the form of a brown resin.

Yield: 0.500 g $^1$H NMR: δ [CDCl$_3$] 1.11–1.27 (m, 9H), 2.13 (m, 2H), 2.45 (m, 2H), 2.68 (m, 2H), 3.17 (q, 2H), 3.45 (q, 2H), 3.70 (q, 2H), 5.29 (s, 2H), 6.07 (m, 1H), 7.80 (d, 1H), 8.00 (d, 1H)

Step 5: 2-(2-Chloro-3-(N,N-diethylaminocarbonylmethoxy)-4-ethylsulfonyl-benzoyl)cyclohexane-1,3-dione 0.450 g (approx. 1.00 mmol) of 3-oxo-1-cyclohexenyl 2-chloro-3-(N,N-diethylaminocarbonylmethoxy)-4-ethylsulfonylbenzoate was dissolved in 10 ml of acetonitrile. 3 drops of acetone cyanohydrin and 0.164 g (1.60 mmol) of NEt$_3$ were added. The mixture was stirred for 2 hours at RT, whereupon 0.019 g (0.30 mmol) of KCN were added. After a further 10 hours at RT, the mixture was concentrated and the product was taken up in water and 6 N HCl was added. The mixture was then extracted with $CH_2Cl_2$. After the combined organic phases had been dried over $Na_2SO_4$, concentrated completely and chromatographed on reversed-phase silica gel (eluent: acetonitrile/water gradient), (2-chloro-3-(N,N-diethylaminocarbonyl-methoxy)-4-ethylsulfonylbenzoyl)cyclohexane-1,3-dione was obtained as a colorless viscous oil.

Yield: 0.180 g (approx. 40% of theory) $R_f$: (ethyl acetate): 0.10

$^1$H NMR: δ [CDCl$_3$] 1.17 (t, 6H), 1.27 (t, 3H), 2.05 (m, 2H), 2.47–2.75 (m, 4H), 3.17 (q, 2H), 3.45 (q, 2H), 3.64 (q, 2H), 4.87 (s, 2H), 7.11 (d, 1H), 7.91 (d, 1H)

Process for the Preparation of 2,4-dibromo-3-(aminocarbonylmethoxy)cyclohexane-1,3-dione (tabulated example No. 3.2)

Step 1: Ethyl 2,4-dibromo-3-(aminocarbonylmethoxy)benzoate 0.853 g (6.20 mmol) of $K_2CO_3$, 0.154 g (0.90 mmol) of Kl and 1.000 g (3.10 mmol) of ethyl 2,4-dibromo-3-hydroxybenzoate were introduced into 15 ml of DMF. 0.346 g (3.70 mmol) of chloroacetamide was added at RT, and the mixture was heated for 6 hours at 120° C. The mixture was then poured into water and extracted with diisopropyl ether. The combined organic phases were washed with water, dried over $Na_2SO_4$ and concentrated completely. Drying in an oil-pump vacuum gave ethyl 2,4-dibromo-3-(aminocarbonylmethoxy)benzoate as a brown oil.

Yield: 0.80 g (68% of theory)

$^1$H NMR: δ [CDCl$_3$] 1.20 (t, 3H), 4.20 (q, 2H), 4.39 (s, 2H), 7.43 (d, 1H), 7.60 (d, 1H)

Step 2: 2,4-Dibromo-3-(aminocarbonylmethoxy)benzoic acid 0.700 g (1.80 mmol) of ethyl 2,4-dibromo-3-(aminocarbonylmethoxy)benzoate was dissolved in 15 ml of THF and 15 ml of water, and 0.147 g (3.70 mmol) of NaOH was added. The mixture was stirred for 12 hours at RT and concentrated completely. The residue was taken up in water and 6 N HCl was added. The precipitate which had formed was filtered off with suction and dried. 2,4-dibromo-3-(aminocarbonyl-methoxy)benzoic acid was obtained as a white solid.

Yield: 0.560 g (88% of theory)

$^1$H NMR: [d6-DMSO] 4.51 (s, 2H), 7.43 (d, 1H), 7.75 (d, 1H)

Step 3: 3-Oxo-1-cyclohexenyl 2,4-dibromo-3-(aminocarbonyl methoxy)benzoate 0.400 g (1.10 mmol) of 2,4-dibromo-3-(aminocarbonylmethoxy)benzoic acid, 0.140 g (1.20 mmol) of cyclohexane-1,3-dione, 0.222 g (1.10 mmol) of N'-(3- dimethyl-aminopropyl)-N-ethylcarbodiimide hydrochloride and 0.001 g of DMAP was stirred for 14 hours at RT in 15 ml of $CH_2Cl_2$. The mixture was subsequently diluted with $CH_2Cl_2$ and with 0.5 N HCl, and washed with water, with saturated $NaHCO_3$ solution and again with water. After the combined organic phases have been dried over $Na_2SO_4$ and concentrated completely, 3-oxo-1-cyclohexenyl 2,4-dibromo-3-(aminocarbonylmethoxy)benzoate was obtained as a yellow resin, which had sufficient purity for the subsequent reaction.

Yield: 0.300 g $^1$H NMR: δ [$CDCl_3$] 2.13 (m, 2H), 2.47 (m, 2H), 2.69 (m, 1H), 4.71 (s, 2H), 6.05 (m, 1H), 7.61 (d, 1H), 7.67 (d, 1H)

Step 4: 2,4-Dibromo-3-(aminocarbonylmethoxy)cyclohexane-1,3-dione 0.300 g (approx. 0.70 mmol) of 3-oxo-1-cyclohexenyl 2,4-dibromo-3-(aminocarbonyl-methoxy)benzoate was dissolved in 10 ml of acetonitrile. 3 drops of acetone cyanohydrin and 0.115 g (1.10 mmol) of $NEt_3$ were added. The mixture was stirred for 2 hours at RT, whereupon 0.005 g (0.10 mmol) of KCN were added. After a further 10 h at RT, the mixture was concentrated completely, the residue was taken up in water, and 6 N HCl was added to the mixture. The mixture was subsequently extracted with $CH_2Cl_2$. After the combined organic phases had been dried over $Na_2SO_4$, concentrated completely and chromatographed on reversed-phase silica gel (eluent: acetonitrile/water gradient), (2,4-dibromo-3-(aminocarbonylmethoxy)-cyclohexane-1,3-dione was obtained as a colorless viscous oil.

Yield: 0.040 g (approx. 13% of theory) $R_f$ (ethyl acetate): 0.45

$^1$H NMR: δ [$CDCl_3$] 2.06 (m, 2H), 2.43 (m, 2H), 2.80 (d, 2H), 4.68 (s, 2H), 6.85 (d, 1H), 7.60 (d, 1H)

The examples given in the tables which follow were prepared analagously to abovementioned methods, or else can be prepared analogously to the abovementioned methods.

The abbreviations used herein denote:

| | | | |
|---|---|---|---|
| Bu = butyl | c = cyclo | Et = ethyl | Me = methyl |
| Ph = phenyl | Pr = propyl | m.p. = melting point | EA = ethyl acetate |

TABLE 1

Compounds according to the invention of the formula (I) in which the substituents and symbols have the following meanings:

$R^{1a}$ = Cl   $R^{1b}$ = $SO_2Me$   $R^{1c}$ = H
$R^4$ = OH   $X^3$ = O   Y = $CH_2$
Z = $CH_2$

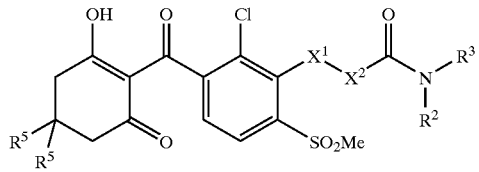

| No. | $X^1$—$X^2$ | —$NR^2R^3$ | $R^5$ | Physical data |
|---|---|---|---|---|
| 1.1 | —$OCH_2$— | —$NH_2$ | H | |
| 1.2 | —$OCH_2$— | —$NH_2$ | Me | |
| 1.3 | —$OCH_2$— | —NHMe | H | |
| 1.4 | —$OCH_2$— | —NHEt | H | |
| 1.5 | —$OCH_2$— | —NH(n-Pr)H | H | |
| 1.6 | —$OCH_2$— | —NH(i-Pr) | H | |

TABLE 1-continued

Compounds according to the invention of the formula (I) in which the substituents and symbols have the following meanings:

$R^{1a}$ = Cl   $R^{1b}$ = $SO_2Me$   $R^{1c}$ = H
$R^4$ = OH   $X^3$ = O   Y = $CH_2$
Z = $CH_2$

| No. | $X^1$—$X^2$ | —$NR^2R^3$ | $R^5$ | Physical data |
|---|---|---|---|---|
| 1.7 | —$OCH_2$— | —$NH(CH_2CH=CH_2)$ | H | |
| 1.8 | —$OCH_2$— | —NH(c-Pr) | H | |
| 1.9 | —$OCH_2$— | —$NH(CH_2$-c-Pr) | H | |
| 1.10 | —$OCH_2$— | —NH(c-Bu) | H | |
| 1.11 | —$OCH_2$— | —NH(c-pentyl) | Me | |
| 1.12 | —$OCH_2$— | —NH(c-hexyl) | H | |
| 1.13 | —$OCH_2$— | —NH(Ph) | H | |
| 1.14 | —$OCH_2$— | —NH(2,4-$Cl_2$Ph) | H | |
| 1.15 | —$OCH_2$— | —$N(Me)_2$ | H | $R_f$ (EA): 0.07 |
| 1.16 | —$OCH_2$— | —$N(Et)_2$ | H | $R_f$ (EA): 0.39 |
| 1.17 | —$OCH_2$— | —$N(i-Pr)_2$ | H | $R_f$ (EA): 0.11 |
| 1.18 | —$OCH_2$— | —N(Me)OMe | H | |
| 1.19 | —$OCH_2$— | —$N(CH_2CH=CH_2)_2$ | H | $R_f$ (EA): 0.33 |
| 1.20 | —$OCH_2$— | —$N(c-Pr)_2$ | H | |
| 1.21 | —$OCH_2$— | —$N(CH_2$-c-Pr$)_2$ | H | |
| 1.22 | —$OCH_2$— | —$N(c-Bu)_2$ | H | |
| 1.23 | —$OCH_2$— | —$N(c-pentyl)_2$ | H | |
| 1.24 | —$OCH_2$— | —$N(c-hexyl)_2$ | H | |
| 1.25 | —$OCH_2$— | —N(Et)Ph | H | |
| 1.26 | —$OCH_2$— | —$NPh_2$ | H | |
| 1.27 | —$OCH_2$— | —$N(2,4-Cl_2-Ph)_2$ | H | |
| 1.28 | —$OCH_2$— | —N(Ph)Me | H | $R_f$ (EA): 0.08 |
| 1.29 | —$OCH_2$— | —N(Ph)i-Pr | H | $R_f$ (EA): 0.09 |
| 1.30 | —$OCH_2$— | pyrrolidin-1-yl | H | $R_f$ (EA): 0.04 |
| 1.31 | —$OCH_2$— | piperidin-1-yl | H | $R_f$ (EA): 0.07 |
| 1.32 | —$OCH_2$— | morpholin-4-yl | H | |
| 1.33 | —$OCH_2CH_2$— | —$NH_2$ | H | |
| 1.34 | —$OCH_2CH_2$— | —NHMe | H | |
| 1.35 | —$OCH_2CH_2$— | —NHEt | H | |
| 1.36 | —$OCH_2CH_2$— | —NH(n-Pr) | H | |
| 1.37 | —$OCH_2CH_2$— | —NH(i-Pr) | H | |
| 1.38 | —$OCH_2CH_2$— | —$NH(CH_2CH=CH_2)$ | H | |
| 1.39 | —$OCH_2CH_2$— | —NH(c-Pr) | H | |
| 1.40 | —$OCH_2CH_2$— | —$NH(CH_2$-c-Pr) | H | |
| 1.41 | —$OCH_2CH_2$— | —NH(c-Bu) | H | |
| 1.42 | —$OCH_2CH_2$— | —NH(c-pentyl) | Me | |
| 1.43 | —$OCH_2CH_2$— | —NH(c-hexyl) | H | |
| 1.44 | —$OCH_2CH_2$— | —NH(Ph) | H | |
| 1.45 | —$OCH_2CH_2$— | —NH(2,4-$Cl_2$Ph) | H | |
| 1.46 | —$OCH_2CH_2$— | —$NMe_2$ | H | |
| 1.47 | —$OCH_2CH_2$— | —$NEt_2$ | H | |
| 1.48 | —$OCH_2CH_2$— | —$N(i-Pr)_2$ | H | |
| 1.49 | —$OCH_2CH_2$— | —N(Me)OMe | H | |
| 1.50 | —$OCH_2CH_2$— | —$N(CH_2CH=CH_2)_2$ | H | |
| 1.61 | —$OCH_2CH_2$— | —$N(c-Pr)_2$ | H | |
| 1.62 | —$OCH_2CH_2$— | —$N(CH_2$-c-Pr$)_2$ | H | |
| 1.63 | —$OCH_2CH_2$— | —$N(c-Bu)_2$ | H | |
| 1.64 | —$OCH_2CH_2$— | —$N(c-pentyl)_2$ | H | |

TABLE 1-continued

Compounds according to the invention of the formula (I) in which the substituents and symbols have the following meanings:

R$^{1a}$ = Cl    R$^{1b}$ = SO$_2$Me    R$^{1c}$ = H
R$^4$ = OH    X$^3$ = O    Y = CH$_2$
Z = CH$_2$

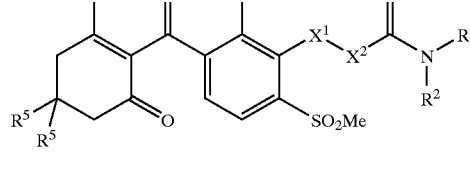

| No. | X$^1$—X$^2$ | —NR$^2$R$^3$ | R$^5$ | Physical data |
|---|---|---|---|---|
| 1.65 | —OCH$_2$CH$_2$— | —N(c-hexyl)$_2$ | H | |
| 1.66 | —OCH$_2$CH$_2$— | —N(Et)Ph | H | |
| 1.67 | —OCH$_2$CH$_2$— | —NPh$_2$ | H | |
| 1.68 | —OCH$_2$CH$_2$— | —N(2,4-Cl$_2$-Ph)$_2$ | H | |
| 1.69 | —OCH$_2$CH$_2$— | —N(Ph)Me | H | |
| 1.70 | —OCH$_2$CH$_2$— | —N(Ph)Me | Me | |
| 1.71 | —OCH$_2$CH$_2$— | —N(Ph)i-Pr | H | |
| 1.72 | —OCH$_2$CH$_2$— | 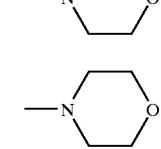 | H | |
| 1.73 | —OCH$_2$CH$_2$— | (piperidine) | H | |
| 1.74 | —OCH$_2$CH$_2$— | (morpholine) | H | |
| 1.75 | —OCH$_2$CH=CH— | —NH$_2$ | H | |
| 1.76 | —OCH$_2$CH=CH— | —NHMe | H | |
| 1.77 | —OCH$_2$CH=CH— | —NHEt | H | |
| 1.78 | —OCH$_2$CH=CH— | —NH(n-Pr) | H | |
| 1.79 | —OCH$_2$CH=CH— | —NH(i-Pr) | H | |
| 1.80 | —OCH$_2$CH=CH— | —NH(CH$_2$CH=CH$_2$) | H | |
| 1.81 | —OCH$_2$CH=CH— | —NH(c-Pr) | H | |
| 1.82 | —OCH$_2$CH=CH— | —NH(CH$_2$-c-Pr) | H | |
| 1.83 | —OCH$_2$CH=CH— | —NH(c-Bu) | H | |
| 1.84 | —OCH$_2$CH=CH— | —NH(c-pentyl) | Me | |
| 1.85 | —OCH$_2$CH=CH— | —NH(c-hexyl) | H | |
| 1.86 | —OCH$_2$CH=CH— | —NH(Ph) | H | |
| 1.87 | —OCH$_2$CH=CH— | —NH(2,4-Cl$_2$Ph) | H | |
| 1.88 | —OCH$_2$CH=CH— | —N(Me)$_2$ | H | |
| 1.89 | —OCH$_2$CH=CH— | —N(Et)$_2$ | H | |
| 1.90 | —OCH$_2$CH=CH— | —N(i-Pr)$_2$ | H | |
| 1.91 | —OCH$_2$CH=CH— | —N(Me)OMe | H | |
| 1.92 | —OCH$_2$CH=CH— | —N(CH$_2$CH=CH$_2$)$_2$ | H | |
| 1.93 | —OCH$_2$CH=CH— | —N(c-Pr)$_2$ | H | |
| 1.94 | —OCH$_2$CH=CH— | —N(CH$_2$-c-Pr)$_2$ | H | |
| 1.95 | —OCH$_2$CH=CH— | —N(c-Bu)$_2$ | H | |
| 1.96 | —OCH$_2$CH=CH— | —N(c-pentyl)$_2$ | H | |
| 1.97 | —OCH$_2$CH=CH— | —N(c-hexyl)$_2$ | H | |
| 1.98 | —OCH$_2$CH=CH— | —N(Et)Ph | H | |
| 1.99 | —OCH$_2$CH=CH— | —NPh$_2$ | H | |
| 1.100 | —OCH$_2$CH=CH— | —N(2,4-Cl$_2$-Ph)$_2$ | H | |
| 1.101 | —OCH$_2$CH=CH— | —N(Ph)Me | H | |
| 1.102 | —OCH$_2$CH=CH— | —N(Ph)i-Pr | H | |
| 1.103 | —OCH$_2$CH=CH— | (pyrrolidine) | H | |
| 1.104 | —OCH$_2$CH=CH— | (piperidine) | H | |
| 1.105 | —OCH$_2$CH=CH— | (morpholine) | H | |
| 1.106 | —OCH$_2$CHCH— | (morpholine) | Me | |
| 1.107 | —OCH$_2$C≡C— | —NH$_2$ | H | |
| 1.108 | —OCH$_2$C≡C— | —NHMe | H | |
| 1.109 | —OCH$_2$C≡C— | —NHEt | H | |
| 1.110 | —OCH$_2$C≡C— | —NH(n-Pr) | H | |
| 1.111 | —OCH$_2$C≡C— | —NH(i-Pr) | H | |
| 1.112 | —OCH$_2$C≡C— | —NH(CH$_2$CH=CH$_2$) | H | |
| 1.113 | —OCH$_2$C≡C— | —NH(c-Pr) | H | |
| 1.114 | —OCH$_2$C≡C— | —NH(CH$_2$-c-Pr) | H | |
| 1.115 | —OCH$_2$C≡C— | —NH(c-Bu) | H | |
| 1.116 | —OCH$_2$C≡C— | —NH(c-pentyl) | H | |
| 1.117 | —OCH$_2$C≡C— | —NH(c-hexyl) | H | |
| 1.118 | —OCH$_2$C≡C— | —NH(Ph) | H | |
| 1.119 | —OCH$_2$C≡C— | —NH(2,4-Cl$_2$Ph) | H | |
| 1.120 | —OCH$_2$C≡C— | —NMe$_2$ | H | |
| 1.121 | —OCH$_2$C≡C— | —NEt$_2$ | H | |
| 1.122 | —OCH$_2$C≡C— | —N(i-Pr)$_2$ | H | |
| 1.123 | —OCH$_2$C≡C— | —N(Me)OMe | Me | |
| 1.124 | —OCH$_2$C≡C— | —N(CH$_2$CH=CH$_2$)$_2$ | H | |
| 1.125 | —OCH$_2$C≡C— | —N(c-Pr)$_2$ | H | |
| 1.126 | —OCH$_2$C≡C— | —N(CH$_2$-c-Pr)$_2$ | H | |
| 1.127 | —OCH$_2$C≡C— | —N(c-Bu)$_2$ | H | |
| 1.128 | —OCH$_2$C≡C— | —N(c-pentyl)$_2$ | H | |
| 1.129 | —OCH$_2$C≡C— | —N(c-hexyl)$_2$ | H | |
| 1.130 | —OCH$_2$C≡C— | —N(Et)Ph | H | |
| 1.131 | —OCH$_2$C≡C— | —NPh$_2$ | H | |
| 1.132 | —OCH$_2$C≡C— | —N(2,4-Cl$_2$-Ph)$_2$ | H | |
| 1.133 | —OCH$_2$C≡C— | —N(Ph)Me | H | |
| 1.134 | —OCH$_2$C≡C— | —N(Ph)i-Pr | H | |
| 1.135 | —OCH$_2$C≡C— | (pyrrolidine) | H | |
| 1.136 | —OCH$_2$C≡C— | (piperidine) | H | |
| 1.137 | —OCH$_2$C≡C— | (morpholine) | H | |

TABLE 1-continued

Compounds according to the invention of the formula (I) in which the substituents and symbols have the following meanings:

$R^{1a}$ = Cl, $R^{1b}$ = $SO_2Me$, $R^{1c}$ = H
$R^4$ = OH, $X^3$ = O, Y = $CH_2$
Z = $CH_2$

| No. | $X^1$—$X^2$ | —$NR^2R^3$ | $R^5$ | Physical data |
|---|---|---|---|---|
| 1.138 | —$OCH_2$— | —$NEt_2$ | Me | $R_f$ (EA): 0.60 |
| 1.139 | —$OCH_2$— | —NMeEt | H | $R_f$ (EA): 0.21 |
| 1.140 | —$OCH_2$— | —NMe($CH_2$)Ph | H | $R_f$ (EA): 0.20 |
| 1.141 | —$OCH_2$— | (N-methylindoline) | H | $R_f$ (EA): 0.12 |
| 1.142 | —$OCH_2$— | (N-methylisoindoline) | H | $R_f$ (EA): 0.04 |
| 1.143 | —$OCH_2$— | (N-methyltetrahydroquinoline) | H | $R_f$ (EA): 0.11 |
| 1.144 | —$OCH_2$— | (N-methyltetrahydroisoquinoline) | H | $R_f$ (EA): 0.07 |

TABLE 2

Compounds of the formula (I) according to the invention in which the substituents and symbols have the following meanings:

$R^{1a}$ = Cl, $R^{1b}$ = $SO_2Me$, $R^{1c}$ = H
$X^3$ = O, Y = $CH_2$, Z = $CH_2$

| No. | $X^1$—$X^2$ | —$NR^2R^3$ | $R^4$ | Physical data |
|---|---|---|---|---|
| 2.1 | —$OCH_2$— | —$NH_2$ | O-Ph | |
| 2.2 | —$OCH_2$— | —$NH_2$ | S-allyl | |
| 2.3 | —$OCH_2$— | —NH(i-Pr) | O-Et | |
| 2.4 | —$OCH_2$— | —NH($CH_2CH=CH_2$) | O-Ph | |
| 2.5 | —$OCH_2$— | —NH(c-Pr) | S-Ph | |
| 2.6 | —$OCH_2$— | —NH(c-hexyl) | O-Ph | |
| 2.7 | —$OCH_2$— | —NH(2,4-$Cl_2$Ph) | S-Ph | |
| 2.8 | —$OCH_2$— | —$NMe_2$ | S-Ph | |
| 2.9 | —$OCH_2$— | —$NEt_2$ | S-allyl | |
| 2.10 | —$OCH_2$— | —N($CH_2CH=CH_2$)$_2$ | O-Et | |
| 2.11 | —$OCH_2$— | —N(Et)v-hexyl | O-Et | |
| 2.12 | —$OCH_2$— | —N(Ph)i-Pr | S-Ph | |
| 2.13 | —$OCH_2$— | pyrrolidin-1-yl | O-Ph | |
| 2.14 | —$OCH_2$— | morpholin-4-yl | S-Ph | |
| 2.15 | —$OCH_2CH_2$— | —$NH_2$ | O-Ph | |
| 2.16 | —$OCH_2CH_2$— | —$NMe_2$ | S-allyl | |
| 2.17 | —$OCH_2CH_2$— | —NH($CH_2$-c-Pr) | S-Ph | |
| 2.18 | —$OCH_2CH_2$— | —N($CH_2CH=CH_2$)$_2$ | O-Et | |
| 2.19 | —$OCH_2CH_2$— | morpholin-4-yl | S-Ph | |
| 2.20 | —$OCH_2CH=CH$— | —$NH_2$ | O-Ph | |
| 2.21 | —$OCH_2CH=CH$— | —$NMe_2$ | S-allyl | |
| 2.22 | —$OCH_2CH=CH$— | —NH($CH_2$-c-Pr) | S-Ph | |
| 2.23 | —$OCH_2CH=CH$— | —N($CH_2CH=CH_2$)$_2$ | O-Et | |
| 2.24 | —$OCH_2CH=CH$— | morpholin-4-yl | S-Ph | |
| 2.25 | —$OCH_2C\equiv C$— | —$NH_2$ | O-Ph | |
| 2.26 | —$OCH_2C\equiv C$— | —$NMe_2$ | S-allyl | |
| 2.27 | —$OCH_2C\equiv C$— | —NH($CH_2$-c-Pr) | S-Ph | |
| 2.28 | —$OCH_2C\equiv C$— | —N($CH_2CH=CH_2$)$_2$ | O-Et | |
| 2.29 | —$OCH_2C\equiv C$— | morpholin-4-yl | S-Ph | |

TABLE 3

Compounds of the formula (I) according to the invention in which the substituents and symbols have the following meanings:

$R^{1c}$ = H $\quad$ $X^3$ = O $\quad$ $R^4$ = OH
Y = $CH_2$ $\quad$ Y = $CH_2$ $\quad$ Z = $CH_2$

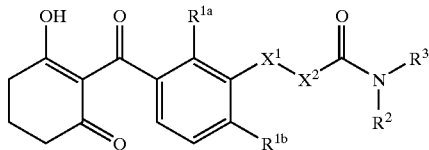

| No. | $R^{1a}$ | $R^{1b}$ | $X^1$—$X^2$ | —$NR^2R^3$ | Physical data |
|---|---|---|---|---|---|
| 3.1 | Cl | Cl | —$OCH_2$— | —$NH_2$ | $R_f$ (EA): 0.04 |
| 3.2 | Br | Br | —$OCH_2$— | —$NH_2$ | $R_f$ (EA): 0.04 |
| 3.3 | Cl | Cl | —$OCH_2$— | —NHMe | |
| 3.4 | Br | Br | —$OCH_2$— | —NHMe | |
| 3.5 | Cl | Cl | —$OCH_2$— | —NHEt | |
| 3.6 | Me | $SO_2Me$ | —$OCH_2$— | —NHEt | |
| 3.7 | Cl | Cl | —$OCH_2$— | —$NMe_2$ | $R_f$ (EA): 0.20 |
| 3.8 | Cl | $SO_2Et$ | —$OCH_2$— | —$NMe_2$ | $R_f$ (EA): 0.08 |
| 3.9 | Cl | Cl | —$OCH_2$— | —$NEt_2$ | $R_f$ (EA): 0.45 |
| 3.10 | Cl | $SO_2Et$ | —$OCH_2$— | —$NEt_2$ | $R_f$ (EA): 0.10 |
| 3.11 | Br | Br | —$OCH_2$— | —$NH(CH_2$-c-Pr) | |
| 3.12 | Cl | $SO_2Et$ | —$OCH_2$— | —N(morpholine) | |
| 3.13 | Cl | Cl | —$OCH_2$— | —N(Me)OMe | |
| 3.14 | Me | $SO_2Et$ | —$OCH_2$— | —N(Me)OMe | |
| 3.15 | Br | Br | —$OCH_2$— | —N(Me)Ph | |
| 3.16 | Cl | Cl | —$OCH_2CH_2$— | —$NH_2$ | |
| 3.17 | Br | Br | —$OCH_2CH_2$— | —$NH_2$ | |
| 3.18 | Cl | Cl | —$OCH_2CH_2$— | —NHMe | |
| 3.19 | Br | Br | —$OCH_2CH_2$— | —NHMe | |
| 3.20 | Cl | Cl | —$OCH_2CH_2$— | —NHEt | |
| 3.21 | Me | $SO_2Me$ | —$OCH_2CH_2$— | —NHEt | |
| 3.22 | Cl | Cl | —$OCH_2CH_2$— | —$NMe_2$ | |
| 3.23 | Cl | $SO_2Et$ | —$OCH_2CH_2$— | —$NMe_2$ | |
| 3.24 | Cl | Cl | —$OCH_2CH_2$— | —$NEt_2$ | |
| 3.25 | Cl | $SO_2Et$ | —$OCH_2CH_2$— | —$NEt_2$ | |
| 3.26 | Br | Br | —$OCH_2CH_2$— | —$NH(CH_2$-c-Pr) | |
| 3.27 | Cl | $SO_2Et$ | —$OCH_2CH_2$— | —N(morpholine) | |
| 3.28 | Cl | Cl | —$OCH_2CH_2$— | —N(Me)OMe | |
| 3.29 | Me | $SO_2Et$ | —$OCH_2CH_2$— | —N(Me)OMe | |
| 3.30 | Br | Br | —$OCH_2CH_2$— | —N(Me)Ph | |
| 3.31 | Cl | Cl | —$OCH_2CH=CH$— | —$NH_2$ | |
| 3.32 | Br | Br | —$OCH_2CH=CH$— | —$NH_2$ | |
| 3.33 | Cl | Cl | —$OCH_2CH=CH$— | —NHMe | |
| 3.34 | Br | Br | —$OCH_2CH=CH$— | —NHMe | |
| 3.35 | Cl | Cl | —$OCH_2CH=CH$— | —NHEt | |
| 3.36 | Me | $SO_2Me$ | —$OCH_2CH=CH$— | —NHEt | |
| 3.37 | Cl | Cl | —$OCH_2CH=CH$— | —$NMe_2$ | |
| 3.38 | Cl | $SO_2Et$ | —$OCH_2CH=CH$— | —$NMe_2$ | |
| 3.39 | Cl | Cl | —$OCH_2CH=CH$— | —$NEt_2$ | |
| 3.40 | Cl | $SO_2Et$ | —$OCH_2CH=CH$— | —$NEt_2$ | |
| 3.41 | Br | Br | —$OCH_2CH=CH$— | —$NH(CH_2$-c-Pr) | |
| 3.42 | Cl | $SO_2Et$ | —$OCH_2CH=CH$— | —N(morpholine) | |
| 3.43 | Cl | Cl | —$OCH_2CH=CH$— | —N(Me)OMe | |
| 3.44 | Me | $SO_2Et$ | —$OCH_2CH=CH$— | —N(Me)OMe | |
| 3.45 | Br | Br | —$OCH_2CH=CH$— | —N(Me)Ph | |
| 3.46 | Cl | Cl | —$OCH_2C\equiv C$— | —$NH_2$ | |
| 3.47 | Br | Br | —$OCH_2C\equiv C$— | —$NH_2$ | |
| 3.48 | Cl | Cl | —$OCH_2C\equiv C$— | —NHMe | |

TABLE 3-continued

Compounds of the formula (I) according to the invention in which the substituents and symbols have the following meanings:

$R^{1c} = H$     $X^3 = O$     $R^4 = OH$
$Y = CH_2$     $Y = CH_2$     $Z = CH_2$

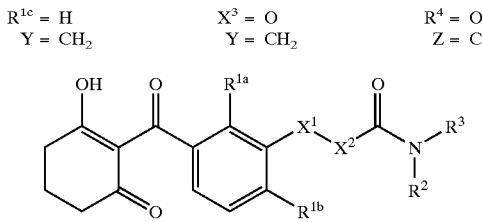

| No. | $R^{1a}$ | $R^{1b}$ | $X^1$—$X^2$ | —$NR^2R^3$ | Physical data |
|---|---|---|---|---|---|
| 3.49 | Br | Br | —OCH$_2$C≡C— | —NHMe | |
| 3.50 | Cl | Cl | —OCH$_2$C≡C— | —NHEt | |
| 3.51 | Me | SO$_2$Me | —OCH$_2$C≡C— | —NHEt | |
| 3.52 | Cl | Cl | —OCH$_2$C≡C— | —NMe$_2$ | |
| 3.53 | Cl | SO$_2$Et | —OCH$_2$C≡C— | —NMe$_2$ | |
| 3.54 | Cl | Cl | —OCH$_2$C≡C— | —NEt$_2$ | |
| 3.55 | Cl | SO$_2$Et | —OCH$_2$C≡C— | —NEt$_2$ | |
| 3.56 | Br | Br | —OCH$_2$C≡C— | —NH(CH$_2$-c-Pr) | |
| 3.57 | Cl | SO$_2$Et | —OCH$_2$C≡C— | ![morpholine] | |
| 3.58 | Cl | Cl | —OCH$_2$C≡C— | —N(Me)OMe | |
| 3.59 | Me | SO$_2$Et | —OCH$_2$C≡C— | —N(Me)OMe | |
| 3.60 | Br | Br | —OCH$_2$C≡C— | —N(Me)Ph | |
| 3.61 | Cl | SO$_2$Et | —OCH$_2$— | —NH$_2$ | $R_f$ (EA): 0.02 |
| 3.62 | Cl | Cl | —OCH$_2$— | —NH(isopropyl) | $R_f$ (EA): 0.26 |
| 3.63 | Cl | Cl | —OCH$_2$— | —NH(CH$_2$CH=CH$_2$) | $R_f$ (EA): 0.43 |
| 3.64 | Br | Br | —OCH$_2$— | —NMe$_2$ | $R_f$ (EA): 0.07 |
| 3.65 | Br | Br | —OCH$_2$— | —NEt$_2$ | $R_f$ (EA): 0.37 |
| 3.66 | Cl | Cl | —OCH$_2$— | —N(n-Prl)$_2$ | $R_f$ (EA): 0.13 |
| 3.67 | Br | Br | —OCH$_2$— | —N(n-Pr)$_2$ | $R_f$ (EA): 0.14 |
| 3.68 | Cl | SO$_2$Et | —OCH$_2$— | —N(n-Pr)$_2$ | $R_f$ (EA): 0.06 |
| 3.69 | Cl | Cl | —OCH$_2$— | —N(i-Pr)$_2$ | $R_f$ (EA): 0.15 |
| 3.70 | Br | Br | —OCH$_2$— | —N(i-Pr)$_2$ | $R_f$ (EA): 0.17 |
| 3.71 | Cl | SO$_2$Et | —OCH$_2$— | —N(i-Pr)$_2$ | $R_f$ (EA): 0.10 |
| 3.72 | Cl | Cl | —OCH$_2$— | —N(CH$_2$CH=CH$_2$)$_2$ | $R_f$ (EA): 0.55 |
| 3.73 | Br | Br | —OCH$_2$— | —N(CH$_2$CH=CH$_2$)$_2$ | $R_f$ (EA): 0.40 |
| 3.74 | Cl | Cl | —OCH$_2$— | —NMeEt | $R_f$ (EA): 0.25 |
| 3.75 | Br | Br | —OCH$_2$— | —NMeEt | $R_f$ (EA): 0.30 |
| 3.76 | Cl | SO$_2$Et | —OCH$_2$— | —NMeEt | $R_f$ (EA): 0.21 |
| 3.77 | Cl | Cl | —OCH$_2$— | —NMe(CH$_2$Ph) | $R_f$ (EA): 0.16 |
| 3.78 | Br | Br | —OCH$_2$— | —NMe(CH$_2$Ph) | $R_f$ (EA): 0.14 |
| 3.79 | Cl | SO$_2$Et | —OCH$_2$— | —NMe(CH$_2$Ph) | $R_f$ (EA): 0.09 |
| 3.80 | Cl | Cl | —OCH$_2$— | —N(Ph)Me | $R_f$ (EA): 0.15 |
| 3.81 | Br | Br | —OCH$_2$— | —N(Ph)Me | $R_f$ (EA): 0.14 |
| 3.82 | Cl | SO$_2$Et | —OCH$_2$— | —N(Ph)Me | $R_f$ (EA): 0.08 |
| 3.83 | Cl | Cl | —OCH$_2$— | —N(Ph)(i-Pr) | $R_f$ (EA): 0.18 |
| 3.84 | Br | Br | —OCH$_2$— | —N(Ph)(i-Pr) | $R_f$ (EA): 0.18 |
| 3.85 | Cl | SO$_2$Et | —OCH$_2$— | —N(Ph)(i-Pr) | $R_f$ (EA): 0.11 |
| 3.86 | Cl | Cl | —OCH$_2$— | (N-pyrrolidinyl) | $R_f$ (EA): 0.06 |
| 3.87 | Br | Br | —OCH$_2$— | (N-pyrrolidinyl) | $R_f$ (EA): 0.04 |
| 3.88 | Cl | SO$_2$Et | —OCH$_2$— | (N-pyrrolidinyl) | $R_f$ (EA): 0.02 |
| 3.89 | Cl | Cl | —OCH$_2$— | (N-piperidinyl) | $R_f$ (EA): 0.06 |

TABLE 3-continued

Compounds of the formula (I) according to the invention in which the substituents and symbols have the following meanings:

R¹ᶜ = H    X³ = O    R⁴ = OH
Y = CH₂    Y = CH₂   Z = CH₂

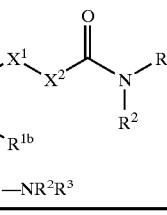

| No. | R¹ᵃ | R¹ᵇ | X¹—X² | —NR²R³ | Physical data |
|---|---|---|---|---|---|
| 3.90 | Br | Br | —OCH₂— | 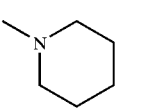 | $R_f$ (EA): 0.08 |
| 3.91 | Cl | SO₂Et | —OCH₂— | | $R_f$ (EA): 0.09 |
| 3.92 | Cl | Cl | —OCH₂— | 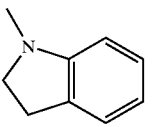 | $R_f$ (EA): 0.17 |
| 3.93 | Br | Br | —OCH₂— | | $R_f$ (EA): 0.17 |
| 3.94 | Cl | SO₂Et | —OCH₂— | | $R_f$ (EA): 0.08 |
| 3.95 | Cl | Cl | —OCH₂— | 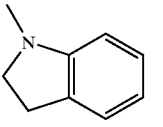 | $R_f$ (EA): 0.09 |
| 3.96 | Br | Br | —OCH₂— | | $R_f$ (EA): 0.10 |
| 3.97 | Cl | SO₂Et | —OCH₂— | | $R_f$ (EA): 0.06 |
| 3.98 | Br | Br | —OCH₂— | 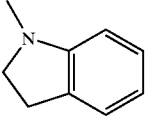 | $R_f$ (EA): 0.15 |
| 3.99 | Cl | SO₂Et | —OCH₂— | | $R_f$ (EA): 0.12 |

TABLE 3-continued

Compounds of the formula (I) according to the invention in which the substituents and symbols have the following meanings:

$R^{1c} = H$     $X^3 = O$     $R^4 = OH$
$Y = CH_2$     $Y = CH_2$     $Z = CH_2$

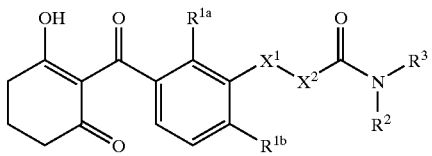

| No. | $R^{1a}$ | $R^{1b}$ | $X^1$—$X^2$ | —$NR^2R^3$ | Physical data |
|---|---|---|---|---|---|
| 3.100 | Cl | Cl | —OCH$_2$— |  | $R_f$ (EA): 0.13 |
| 3.101 | Cl | SO$_2$Et | —OCH$_2$— |  | $R_f$ (EA): 0.04 |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-Dispersible Granules

Water-dispersible granules are obtained by mixing

| | |
|---|---|
| 75 | parts by weight of a compound of the formula (I), |
| 10 | parts by weight calcium ligninsulfonate, |
| 5 | parts by weight sodium lauryl sulfate, |
| 3 | parts by weight polyvinyl alcohol and |
| 7 | parts by weight kaolin | grinding the mixture in a pinned-disk mill and granulating the powder in a fluidized bed by spraying on water as granulation liquid.

Water-dispersible granules are also obtained by homogenizing and precomminuting, in a colloid mill,

| | |
|---|---|
| 25 | parts by weight of a compound of the formula (I), |
| 5 | parts by weight sodium 2,2'-dinaphthylmethane-6,6'-disulfonate, |
| 2 | parts by weight sodium oleoylmethyltauride, |
| 1 | parts by weight polyvinyl alcohol, |
| 17 | parts by weight calcium carbonate and |
| 50 | parts by weight water, | subsequently grinding the mixture in a bead mill, and atomizing and drying the resulting suspension in a spray tower by means of a single-substance nozzle.

C. BIOLOGICAL EXAMPLES

1. Pre-Emergence Herbicidal Action

Seeds of mono- and dicotyledonous harmful plants are placed in sandy loam in cardboard pots and covered with soil. The compounds according to the invention, which are formulated in the form of wettable powders or emulsion concentrates, are then applied to the surface of the soil cover as aqueous suspension or emulsion at a dosage rate stated in table B1 with an application rate of 600 to 800 l of water per ha (converted). After the treatment, the pots are placed into a greenhouse and kept under good growth conditions for the harmful plants. The damage to the plants or their emergence is scored visually after the test plants have emerged after an experimental time of 3 to 4 weeks by comparison with untreated controls. As demonstrated by the results of this table, the selected compounds according to the invention have an outstanding activity against a broad spectrum of economically important monocotyledonous and dicotyledonous harmful plants.

2. Post-Emergence Herbicidal Action

Seeds of mono- and dicotyledonous harmful plants are placed in sandy loam in cardboard pots, covered with soil and grown in the greenhouse under good growth conditions. 2 to 3 weeks after sowing, the test plants are treated in the three-leaf stage. The compounds according to the invention, which are formulated as wettable powders or as emulsion concentrates, are sprayed at a dosage rate stated in table B2 to the surface of the green plant parts at an application rate of 600 to 800 l of water per ha (converted). After the test plants have been left to stand in the greenhouse for approx. 3 to 4 weeks under optimal growth conditions, the effect of the compounds is scored by comparison with compounds of the prior art. As demonstrated by the results of the table, the chosen compounds according to the invention have an outstanding activity against the broad spectrum of economically important monocotyledonous and bicotyledonous harmful plants.

3. Plant Tolerance

In further greenhouse experiments, seeds of barley and of monocotyledonous and dicotyledonous harmful plants are placed in sandy loam, covered with soil and placed in the greenhouse until the plants have developed two to three true leaves. Then, they are treated with the compounds of the formula (I) according to the invention as described above under item 2. Four to five weeks after the application and after having been left to stand in the greenhouse, visual scoring reveals that the compounds according to the invention are outstandingly well tolerated by important crop plants, in particular wheat, maize and rice.

The abbreviations used in the following comparative tables mean:

| | | | |
|---|---|---|---|
| AMARE | Amaranthus retroflexus | CYPSE | Cyperus serotinus |
| MOOVA | Monochoria vaginalis | ORYSP | Oryza sativa |
| SAGPY | Sagittaria pygmaea | SINAL | Sinapis arvensis |
| STEME | Stellaria media | | |

TABLE B1 pre-emergence herbicidal action

| | | Action against harmful plants | | |
|---|---|---|---|---|
| Compound No. | Dosage [g a.i./ha] | AMARE | SINAL | STEME |
| 1.28 | 320 | 90% | 90% | 90% |
| 3.9 | 320 | 90% | 80% | 90% |
| 3.65 | 320 | 90% | 80% | 90% |

TABLE B2 post-emergence herbicidal action

| | | Action against harmful plants | | |
|---|---|---|---|---|
| Compound No. | Dosage [g a.i./ha] | AMARE | SINAL | STEME |
| 3.9 | 320 | 80% | 90% | 100% |
| 3.65 | 320 | 80% | 90% | 100% |
| 3.87 | 320 | 70% | 80% | 90% |

TABLE B3 post-emergence action

| Compound No. | Dosage [g a.i./ha] | Crop plant damage ORYSP | Action against harmful plants | | |
|---|---|---|---|---|---|
| | | | CYPSE | MOOVA | SAGPY |
| 3.9 | 90 | 0% | 95% | 95% | 90% |
| 3.65 | 50 | 0% | 99% | 99% | 80% |

We claim:

1. A compound of the formula (I) or a salt thereof

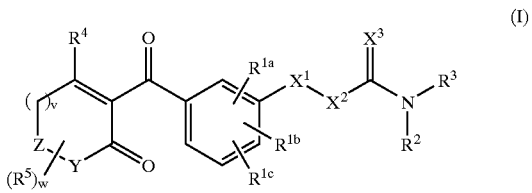

in which

X¹ is a divalent unit selected from the group consisting of O, S(O)$_n$, N—H and N—R²;

X² is a straight-chain or branched (C$_1$–C$_6$)-alkylene, (C$_2$–C$_6$)-alkenylene or (C$_2$–C$_6$)-alkynylene chain which is substituted by w radicals selected from the group consisting of halogen, cyano and nitro and by v radicals R²;

X³ is oxygen or sulfur;

R$^{1a}$, R$^{1b}$, R$^{1c}$ independently of one another are hydrogen, mercapto, nitro, halogen, cyano, thiocyanato, (C$_1$–C$_6$)-alkyl-CO—O, (C$_1$C$_6$)-alkyl-S(O)$_n$—O, (C$_1$–C$_6$)-alkyl-S(O)$_n$, di-(C$_1$–C$_6$)-alkyl-NH—SO$_2$, (C$_1$–C$_6$)-alkyl-SO$_2$—NH, (C$_1$–C$_6$)-alkyl-NH—CO, (C$_1$–C$_6$)-alkyl-SO$_2$—[(C$_1$–C$_6$)-alkyl]amino, (C$_1$–C$_6$)-alkyl-CO—[(C$_1$–C$_6$)-alkyl]amino, 1,2,4-triazol-1-yl, (C$_1$–C$_6$)-alkyl-O—CH$_2$, (C$_1$–C$_6$)-alkyl-S(O)$_n$—CH$_2$, (C$_1$–C$_6$)-alkyl-NH—CH$_2$, 1,2,4-triazol-1-yl—CH$_2$, or are (C$_1$–C$_6$)-alkyl-(D)$_p$, (C$_2$–C$_6$)-alkenyl-(D)$_p$, (C$_2$–C$_6$)-alkynyl-(D)$_p$, (C$_3$–C$_9$)-cycloalkyl-(D)$_p$, (C$_3$–C$_9$)-cycloalkenyl-(D)$_p$, (C$_1$–C$_6$)-alkyl-cycloalkyl-(D)$_p$, (C$_1$–C$_6$)-alkyl-cycloakenyl-(D)$_P$, each of which is substituted by v radicals selected from the group consisting of cyano, nitro and halogen;

D is oxygen or sulfur;

R², R³ independently of one another are hydrogen, (C$_1$–C$_6$)-alkyl, (C$_2$–C$_6$)-alkenyl, (C$_2$–C$_6$)-alkynyl, (C$_3$–C$_9$)-cycloalkenyl, (C$_1$C$_6$)-alkyl-(C$_3$–C$_9$)-cycloalkyl, (C$_1$C$_6$)-alkyl-(C$_3$–C$_9$)-cycloalkenyl, (C$_2$–C$_6$)-alkenyl-(C$_3$–C$_9$)-cycloalkyl, (C$_2$–C$_6$)-alkenyl-(C$_3$–C$_9$)-cycloalkenyl, (C$_2$–C$_6$)-alkynyl-(C$_3$–C$_9$)-cycloalkyl, (C$_2$–C$_6$)-alkynyl-(C$_3$–C$_9$)-cycloalkenyl, straight-chain or branched [O—C(R$^6$)$_2$]$_w$—[O—C(R$^6$)$_2$]$_x$—R$^6$, (C$_1$–C$_6$)-alkylaryl, (C$_2$–C$_6$)-alkenylaryl, (C$_2$–C$_6$)-alkynylaryl, straight-chain or branched [O—C(R$^6$)$_2$]$_w$-aryl, the abovementioned carbon-containing radicals being substituted by v radicals selected from the group consisting of cyano, nitro and halogen, aryl, heterocyclyl or heteroaryl, each of which is substituted by v radicals selected from the group consisting of cyano, nitro, halogen, (C$_1$–C$_6$)-alkyl-(D)$_p$ and halo-(C$_1$–C$_6$)-alkyl-(D)$_p$, or R² and R³ together with the nitrogen atom to which they are bonded form a 5- or 6-membered, saturated, partially unsaturated or fully unsaturated ring comprising m hetero atoms, in addition to the nitrogen atom that is already bound to R² and R³, selected from the group consisting of oxygen and nitrogen, the 5- or 6-membered ring optionally being benzo-fused to a phenyl ring and being substituted by v radicals selected from the group consisting of cyano, nitro, halogen, (C$_1$–C$_6$)-alkyl-(D)$_p$ and halo-(C$_1$–C$_6$)-alkyl-(D)$_p$ and the fused phenyl ring being substituted by v radicals selected from the group consisting of cyano, nitro and halogen;

$R^4$ is $OR^7$, $(C_1-C_4)$-alkylthio, halo-$(C_1-C_4)$-alkylthio, $(C_2-C_4)$-alkenylthio, halo-$(C_2-C_4)$-alkenylthio, $(C_2-C_4)$-alkenylthio, halo-$(C_2-C_4)$-alkynylthio, $(C_1-C_4)$-alkylsulfinyl, halo-$(C_1-C_4)$-alkylsulfinyl, $(C_2-C_4)$-alkenylsulfinyl, halo-$(C_2-C_4)$-alkenylsulfinyl, $(C_2-C_4)$-alkynlsulfinyl, halo-$(C_2-C_4)$-alkynylsulfinyl, $(C_1-C_4)$-alkylsulfonyl, halo-$(C_1-C_4)$-alkylsulfonyl, $(C_2-C_4)$-alkenylsulfonyl, halo-$(C_2-C_4)$-alkenylsulfonyl, $(C_2-C_4)$-alkynylsulfonyl, halo-$(C_2-C_4)$-alkynylsulfonyl, halogen, cyano, cyanato, thiocyanato or phenylthio;

$R^5$ is hydrogen, tetrahydropyran-3-yl, tetrahydropyran-4-yl, tetrahydrothiopyran-3-yl, $(C_1-C_4)$-alkyl, $(C_1-C_8)$-cycloalkyl, $(C_1-C_4)$-alkoxy, $(C_1-C_4)$-alkoxy-$(C_1-C_4)$-alkyl, $(C_1-C_4)$-alkoxycarbonyl, $(C_1-C_4$alkylthio, phenyl, the eight last-mentioned groups being substituted by v radicals selected from the group consisting of halogen, $(C_1-C_4)$-alkylthio and $(C_1-C_4)$-alkoxy, or two radicals $R^5$ bonded to a joint carbon atom form a chain selected from the group consisting of $OCH_2CH_2O$, $OCH_2CH_2CH_2O$, $SCH_2CH_2S$ and $SCH_2CH_2CH_2S$, this chain being substituted by w methylene groups, or two radicals $R^5$ bonded to directly adjacent carbon atoms, together with the carbon atoms bearing them, form a 3- to 6-membered ring which is substituted by w radicals selected from the group consisting of halogen, $(C_1-C_{b\,4})$-alkyl, $(C_1-C_4)$-alkylthio and $(C_1-C_4)$-alkoxy;

$R^5$ is hydrogen, halogen, cyano or nitro, $(C_1-C_4)$-alkyl, halo-$(C_1-C_4)$-alkyl;

$R^7$ is hydrogen, $(C_1-C_4)$-alkyl, halo-$(C_1-C_4)$-alkyl, $(C_1-C_4)$-alkoxy-$(C_1-C_4)$-alkyl, formyl, $(C_1-C_4)$-alkylcarbonyl, $(C_1-C_4)$-alkoxycarbonyl, $(C_1-C_4)$-alkylaminocarbonyl, di-$(C_1-C_4)$-alkylaminocarbonyl, $(C_1-C_4)$-alkylsulfonyl, halo-$(C_1-C_4)$-alkylsulfonyl, phenyl, benzoyl or phenylsulfonyl, the three last-mentioned groups being substituted by v radicals selected from the group consisting of $(C_1-C_4)$-alkyl, halo-$(C_1-C_4)$-alkyl, $(C_1-C_4)$-alkoxy, halo-$(C_1-C_4)$-alkoxy, halogen, cyano and nitro;

Y is a divalent unit selected from the group consisting of O, S, N—H, N—$(C_1-C_6)$-alkyl, $CHR^5$ and $C(R^5)_2$;

Z is a direct bond or a divalent unit selected from the group consisting of O, S, SO, $SO_2$, N—H, N-alkyl, $CHR^6$ or $C(R^6)_2$;

m and n in each case independently of one another are 0, 1 or 2;

p is independently 0 or 1;

v is independently 0, 1, 2 or 3;

w and x in each case independently of one another are 0, 1, 2, 3 or 4, with the proviso that w and x are not simultaneously zero.

2. A compound as claimed in claim 1, in which $R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl -$(C_3-C_9)$-cycloalkyl, $(C_2-C_6)$-alkynyl, $(C_3-C_9)$-cycloalkenyl, straight-chain or branched $[O—C(R^6)_2]_w—[O—C(R^6)_2]—R^6$, the 12 last-mentioned radicals being substituted by v radicals selected from the group consisting of cyano, nitro and halogen, aryl which is substituted by v radicals selected from the group consisting of cyano, nitro, halogen, $(C_1-C_6)$-alkyl-$(D)_p$ and halo-$(C_1-C_6)$-alkyl-$(D)_p$ or $R^2$ and $R^3$ together with the nitrogen atom to which they are bonded form a 5- or 6-membered, saturated, partially unsaturated or fully unsaturated ring comprising m hetero atoms, in addition to the nitrogen atom that is already bound to $R^2$ and $R^3$, selected from the group consisting of oxygen and nitrogen, which ring is substituted by v radicals selected from the group consisting of cyano, nitro, halogen, $(C_1-C_6)$-alkyl-$(D)_p$ and halo-$(C_1-C_6)$-alkyl-$(D)_p$;

$R^7$ is hydrogen, $(C_1-C_4)$-alkylsulfonyl, halo-$(C_1-C_4)$-alkylsulfonyl, phenyl, benzoyl or phenylsulfonyl, the three last-mentioned groups being substituted by v radicals selected from the group consisting of $(C_1-C_2)$-alkyl, halo-$(C_1-C_2)$-alkyl, $(C_1-C_2)$-alkoxy, halo-$(C_1-C_2)$-alkoxy, halogen, cyano and nitro;

Y is a divalent unit selected from the group consisting of O, N—H, N-$(C_1-C_6)$-alkyl, $CHR^5$ and $C(R^5)_2$, and Z is a divalent unit selected from the group consisting of O, S, $SO_2$, $(C_1-C_6)$-alkyl, $CHR^6$ or $C(R^6)_2$.

3. A compound as claimed in claim 1, in which $X^3$ is oxygen, $R^{1c}$ is hydrogen, and $R^6$ is hydrogen, $(C_1-C_4)$-alkyl or halo-$(C_1-C_4)$-alkyl.

4. A compound as claimed in claim 1, in which $X^1$ is oxygen;

$R^{1a}$ and $R^{1b}$ are in each case bromine, chlorine, fluorine, methyl, methylthio, methoxy, methylsulfonyl, ethylsulfonyl or trifluoromethyl, and $R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_1-C_6)$-alkyl-$(C_3-C_9)$-cycloalkyl, straight-chain or branched $[O—C(R^6)_2]_w—[O—C(R^6)—_2]R^6$ where the 6 last-mentioned radicals are substituted by v radicals selected from the group consisting of cyano, nitro and halogen, are aryl which is substituted by v radicals selected from the group consisting of cyano, nitro, halogen, $(C_1-C_6)$-alkyl-$(D)_p$ and halo-$(C_1-C_6)$-alkyl-$(D)_p$, or $R^2$ and $R^3$ together with the nitrogen atom to which they are bonded form a 5- or 6-membered, saturated, partially unsaturated or fully unsaturated ring comprising in hetero atoms, in addition to the nitrogen atom that is already bound to $R^2$ and $R^3$, selected from the group consisting of oxygen and nitrogen, which ring is substituted by v radicals selected from the group consisting of cyano, nitro, halogen, $(C_1-C_6)$-alkyl-$(D)_p$ and halo-$(C_1-C_6)$-alkyl-$(D)_p$.

5. A compound as claimed in claim 1, in which $R^4$ is $OR^7$, $(C_1-C_4)$-alkylthio, $(C_2-C_4)$-alkenylthio, $(C_1-C_4)$-alkylsulfonyl, halogen, cyano, cyanato, thiocyanato or phenylthio and $R^5$ is hydrogen, $(C_1-C_4)$-alkyl, $(C_1-C_8)$-cycloalkyl, $(C_1-C_4$-alkoxy, $(C_1-C_4$-alkylthio, phenyl, or two radicals $R^5$ bonded to directly adjacent carbon atoms together with the carbon atoms to which they are bonded form a substituted 3- to 6-membered ring.

6. A compound as claimed in claim 1, in which the substituent $R^{1a}$ is in the 2-position of the substituent $R^{1b}$ in the 4-position of the phenyl ring.

7. A compound as claimed in claim 1, in which $R^4$ is $OR^7$;

D is oxygen;

Y and Z are the group $CH_2$, and v and w are in each case independently of one another 0, 1 or 2.

8. A compound as claimed in claim 1, which are not in salt form.

9. A herbicidal composition which comprises a herbicidally active content of at least one compound of the formula (I) as claimed in claim 1.

10. A herbicidal composition as claimed in claim 9 as a mixture with formulation auxiliaries.

11. A method of controlling undesired plants, which comprises applying an effective amount of at least one compound of the formula (I) as claimed in claim 1 to the plants or to the site where the plants are located.

12. A method of using a compound of the formula (I) as claimed in claim 1 for controlling undesired plants, comprising the step of applying the compound to the plants or to the site where the plants are located.

13. The method of use as claimed in claim 12, wherein the compounds of the formula (I) are employed for controlling undesired plants in crops of useful plants.

14. The method of use as claimed in claim 13, wherein the useful plants are transgenic useful plants.

15. A method of controlling undesired plants, which comprises applying an effective amount of a herbicidal composition as claimed in claim 9 to the plants or to the site where the plants are located.

16. A method of controlling undesired plants, which comprises applying an effective amount of a herbicidal composition as claimed in claim 10 to the plants or to the site where the plants are located.

17. A method of using a herbicidal composition as claimed in claim 9 for controlling undesired plants, comprising the step of applying the compound to the plants or to the site where the plants are located.

18. A method of using a herbicidal composition as claimed in claim 10 for controlling undesired plants, comprising the step of applying the compound to the plants or to the site where the plants are located.

* * * * *

UNITED STATES PATENT AND TRADEMARK OFFICE
CERTIFICATE OF CORRECTION

PATENT NO. : 6,774,086 B2
DATED : August 10, 2004
INVENTOR(S) : Thomas Seitz et al.

It is certified that error appears in the above-identified patent and that said Letters Patent is hereby corrected as shown below:

Title page,
Item [56], References Cited, FOREIGN PATENT DOCUMENTS,
"AT 200131666 7/2001" should read -- AU 200131666 7/2001 --.

Column 34,
Line 38, after "$(C_2-C_6)$-alkynyl," insert -- $(C_3-C_9)$-cycloalkyl. --.
Line 39, "$(C_1\ C_6)$" should read -- $(C_1-C_6)$ --.
Line 47, before "aryl" insert -- $[O-C(R^6)_2]_x$- --.

Column 35,
Line 15, "$(C_1-C_2$ alkylthio," should read -- $(C_1-C_2)$-alkylthio, --.
Line 28, "$(C_1-C_{b\ 4})$-alkyl," should read -- $(C_1-C_4)$-alkyl, --.
Line 30, "$R^5$" should read -- $R^6$ --.
Lines 59-60, "$(C_1-C_6)$-alkyl-$(C_3-C_3-C_9)$-cycloalkyl," should read -- $(C_1-C_6)$-alkyl-$(C_3-C_9)$-cycloalkyl, --.
Lines 62-63, "$(C_2-C_6)$-alkynyl, $(C_3-C_9)$-cycloalkenyl," should read -- $(C_2-C_6)$-alkynyl-$(C_3-C_9)$-cycloalkenyl, --.
Line 65, "$[O-C(R^6)_2]_w-[O-C(R^6)-_2]-R^6$" should read -- $[O-C(R^6)_2]_w-[O-C(R^6)-_2]_x-R^6$ --.

Column 36,
Lines 38-39, "$[O-C(R^6)_2]_w-[O-C(R^6)-_2]-R^6$" should read
-- $[O-C(R^6)_2]_w-[O-C(R^6)-_2]_x-R^6$ --.
Line 50, "in hetero" should read -- m hetero --.
Line 61, "$(C_1-C_4$-alkoxy, $(C_1-C_4$-alkythio," should read -- $(C_1-C_4)$-alkoxy, $(C_1-C_4-)$-alkythio, --.

Signed and Sealed this

First Day of March, 2005

JON W. DUDAS
*Director of the United States Patent and Trademark Office*